US006395158B1

United States Patent
King et al.

(10) Patent No.: US 6,395,158 B1
(45) Date of Patent: May 28, 2002

(54) PH SENSOR WITH ELECTRICAL NOISE IMMUNITY

(75) Inventors: Karl L. King; Joseph A. Millhouse, both of Brown Deer, WI (US)

(73) Assignee: GLI International, Milwaukee, WI (US)

(*) Notice: Subject to any disclaimer, the term of this patent is extended or adjusted under 35 U.S.C. 154(b) by 0 days.

(21) Appl. No.: 09/706,954

(22) Filed: Nov. 6, 2000

(51) Int. Cl.[7] .............................................. G01N 27/36
(52) U.S. Cl. ....................... 204/420; 204/400; 204/433; 204/435; 205/787.5
(58) Field of Search ................................ 204/420, 435, 204/433; 205/787.5

(56) References Cited

U.S. PATENT DOCUMENTS

| 2,563,062 A | * | 8/1951 | Perley |
| 3,306,837 A | * | 2/1967 | Riseman et al. ............ 204/420 |
| 3,862,895 A | | 1/1975 | King et al. |
| 4,252,124 A | * | 2/1981 | Maurer et al. .............. 204/435 |
| 4,447,309 A | | 5/1984 | Morioka et al. |
| 4,458,685 A | * | 7/1984 | Hiramoto et al. |
| 4,608,148 A | * | 8/1986 | Frollini et al. |
| 4,891,124 A | * | 1/1990 | Rigdon et al. .............. 204/435 |
| 5,152,882 A | | 10/1992 | Benton |

OTHER PUBLICATIONS

What is pH and How is It Measured? GLI International Sep. 1997.
Merriam–Webster's Collegiate Dictionary, Tenth Edition, Merriam–Webster, Inc. 1994 p. 1223 date unavailable.
Data sheet LRE/400 for Encapsulated Differential pH and ORP Sensors from GLI International date unavailable.
Data sheet PC/200 for 3/4–inch Combination pH and ORP Sensors from GLI International date unavailable.
Data sheet PDS 71–TupH for Model 396/396P/396R Retraction/Submersion/Insertion pH/ORP Sensor from Rosemount Analytical date unavailable.
Data sheet D2. 1134–DS for Meredian II Combination pH Electrodes for L&N 7777 Mounting from Leeds & Northrup date unavailable.

* cited by examiner

Primary Examiner—T. Tung
(74) Attorney, Agent, or Firm—George E. Haas; Quarles & Brady LLP

(57) ABSTRACT

A sensor for measuring pH of a solution includes a housing with an exterior surface for exposure to the solution. A measuring glass electrode within a tubular circuit ground electrode extends through the exterior surface. A reference glass electrode is received in a neutral pH solution in the housing and is coupled by a salt bridge to the exterior surface. An electric circuit within the housing has a first preamplifier connected by a first conductor to the measuring glass electrode and has a second preamplifier connected by a second conductor to the reference glass electrode. The first and second conductors have substantially equal lengths so that ambient electrical noise equally affects signals from the electrodes. The electrical cable that carries output signals from the electric circuit passes through a ferrite sleeve which inhibits high frequency electric noise that is induced in the cable from reaching the electric circuit.

20 Claims, 2 Drawing Sheets

PH SENSOR WITH ELECTRICAL NOISE IMMUNITY

BACKGROUND OF THE INVENTION,

The present invention relates to sensors for continuously measuring the pH of absolution, such as in chemical processing.

A wide variety of types of sensors have been developed to measure the pH of chemical solutions in industrial processes. One type of pH sensor employs a glass electrode in the form of a hollow glass tube containing a solution of a neutral pH (i.e. pH=7.0). A tip of the glass tube that is exposed to the solutions being tested is sensitive to hydrogen ion activity and pH difference across the inner and outer surfaces. An electric wire extends through the wall of the glass tube into the neutral pH solution. The glass electrode is spaced from a metal electrode and. the electrodes are exposed to the solution that has an unknown pH.

The measurement process is predicated on the principle that a hydrated gel layer forms between the outer surface of the glass and the solution being tested. Depending upon the pH of that solution being tested hydrogen ions migrate into or out of the gel layer. For example in an alkaline solution, hydrogen ions migrate out of the gel layer developing a negative charge in that layer. Because the solution inside the glass tube has a constant, neutral pH, an electric potential develops across the glass membrane due to the difference in the inner and outer electric charges. This produces a first electrical signal between the glass and metal electrodes which varies with the pH of the solution.

A second glass electrode is placed within another chemical solution that has a known pH and thus producing a second electrical signal. The unknown pH of the solution being tested can be determined by comparing the two electrical signals.

The pH sensors are commonly used in industrial environments that have significant ambient electrical noise. Depending upon the routing of the conductors between the electrodes and preamplifiers in the processing circuits, the electrical noise can be induced into the electrode signals and applied to the preamplifiers. Even when the preamplifiers are incorporated into the housing for the electrodes, electrical noise can be induced into he conductors that connect the remote sensor to the apparatus that derives the pH measurement, thus adversely effecting accuracy of that measurement.

Therefore it is desirable to provide a sensor which accurately measures pH of the chemical solution under test, and has a relatively high degree of immunity to ambient electrical noise.

SUMMARY OF THE INVENTION

The present invention provides a pH sensor that has a compact housing that contains sensing electrodes and signal preamplifiers. The sensor is designed to limit the effects that ambient electrical noise has of the signals being produced.

The sensor includes a housing with a section having an exterior surface for exposure to the solution being tested. A measuring glass electrode and a circuit ground electrode extend through the exterior surface of the housing section. First and second preamplifiers are mounted within the housing and a first electrical conductor connects the measuring glass electrode to the first preamplifier. A second electrical conductor connects the reference glass electrode to the second preamplifier. The first and second electrical conductors have substantially the same length so that ambient electrical noise equally affects the different signals that the conductors carry.

Another aspect of the invention provides a ferrite sleeve through which passes the electrical cable that carries the output signals from the first and second preamplifiers to remote signal processing circuits.

DETAILED DESCRIPTION OF THE INVENTION

Figure 1:
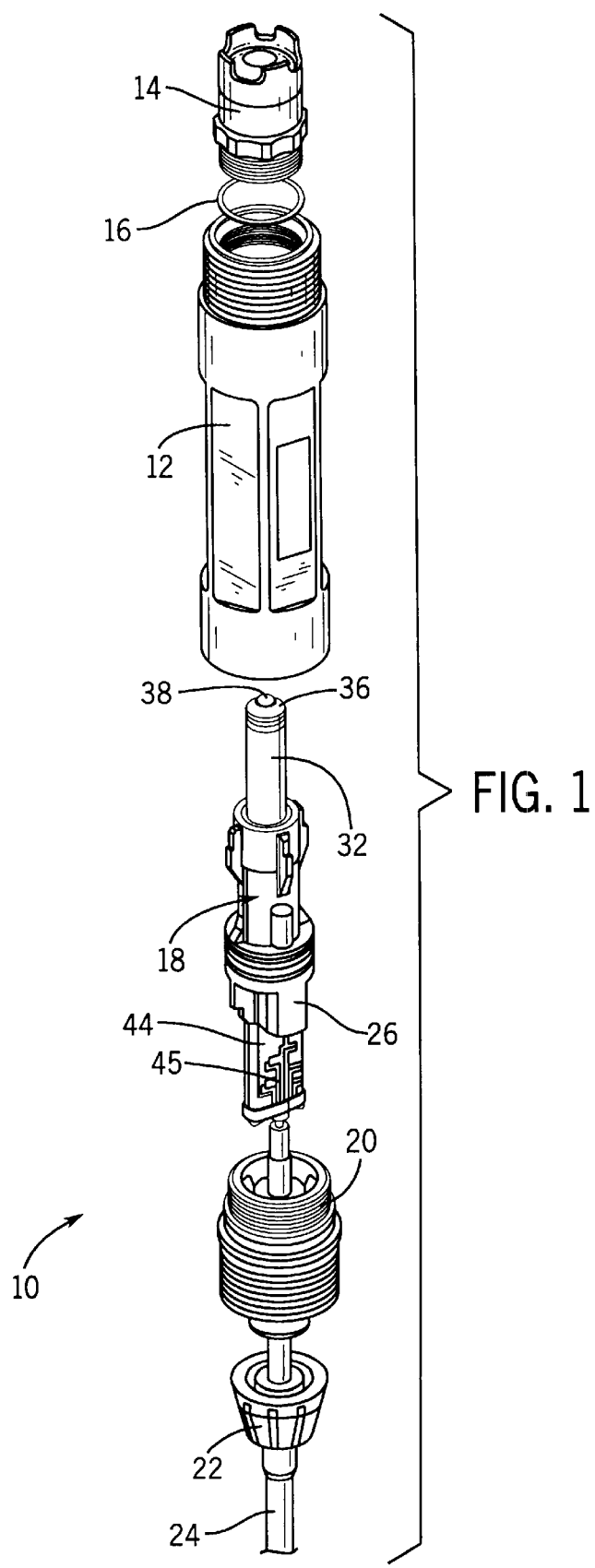
FIG. 1 is an exploded view of a pH sensor according to the present invention.

With initial reference to FIG. 1, a pH sensor 10 has a generally cylindrical housing formed by an outer tube 12 with open ends that are closed by a sensor tip 14 and a plug 20. A sensor tip 14 is threaded into one of the open ends with a resilient ring 16 providing a fluid-tight seal there between. A sensing assembly 18 is located within the outer tube 12 and is held in place by the plug 20 threaded into the opposite end of the outer tube 12. A cap 22 engages the plug 20 and secures an electrical cable 24 which passes through the plug. A strain relief 52 provides protection as the cable 24 emerges from the end cap 24. The outer tube 12, sensor tip 14, plug 20 and cap 22 are formed of electrically non-conductive material, such as a plastic.

Figure 2:
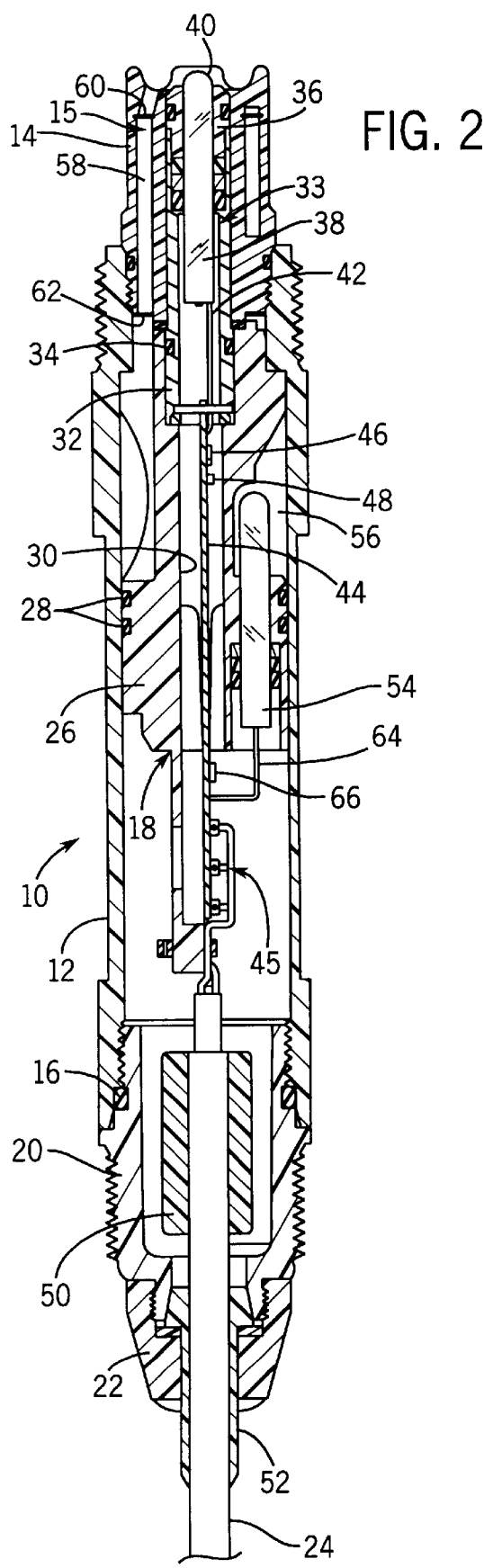
FIG. 2 is a longitudinal cross-sectional view through an assembled pH sensor.

Referring to FIG. 2, the sensing assembly 18 has a plastic support tube 26 which is received within the outer tube 12. O-rings 28 provide fluid-tight seals between the support tube 26 and the inner surface of the outer tube 12. The support tube 26 has an internal cavity 30 extending longitudinally there through. A circuit ground electrode 33 is formed by a metal tube 32 and a tubular terminus 36 and is connected to a printed circuit board 44. The metal tube 32 is received in the internal cavity 30 of the support tube 26 and projects into a central opening in the sensor tip 14. Another O-ring 34, provides a fluid-tight seal between the circuit ground electrode 33 and the support tube. The tubular terminus 36 is force fitted onto an end of the metal tube 32 at an external open end of the sensor tip 14.

Figure 3:
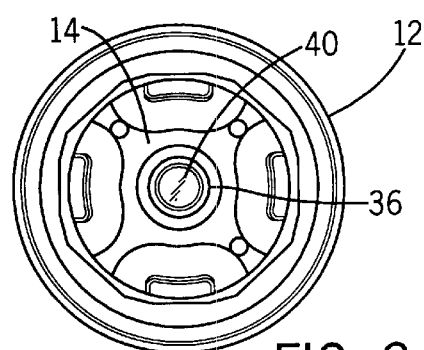
FIG. 3 is a view of the end of the pH sensor which is exposed to the chemical solution being tested.

A measuring glass electrode 38 is located within the circuit ground electrode 33 and terminus electrode 36 and has an exposed tip 40 that projects outwardly from the sensor tip 14. FIG. 3 shows the end of the pH sensor 10 at which the rounded tip 40 of the measuring glass electrode 38 is exposed. During use of the sensor, this end of the pH sensor is placed into the solution being tested. The measuring glass electrode 38 has a conventional design, in that it comprises a hollow sealed glass tube that contains a solution having a neutral pH of 7.0. The rounded tip 40 of the measuring glass electrode is sensitive to hydrogen ion activity as in previous glass electrode used in pH sensors. A first electrical lead 42 passes through the glass tube into the solution and has an external end that is connected to the printed circuit board 44. This structure forms a first half cell between the circuit ground electrode 33 and the first electrical lead 42. The potential that develops across the glass wall at the top 40 of the measuring glass electrode 38 results from the difference between the inner and outer electric charges due to different pH values.

The printed circuit board 44 is secured within the internal cavity 30 6f the support tube 26. The printed circuit board 44 contains the electrical circuitry for pre-amplifying signals produced by components of the pH sensor 10 and sending those signals over the cable 24. In particular, a first pre-amplifier 46 located in close proximity to the connection point of the first electrical lead 42. A temperature sensor 48 is mounted on the printed circuit board in the vicinity of that connection point. The narrow elongated printed circuit board 44 extends through the internal cavity 30 toward the plug 20 where terminals 45 are provided on the printed circuit board for the connection of internal wires from the cable 24. Those internal wires carry electrical power to the printed circuit board and carry the output signals from the preamplifiers and temperature sensor to a conventional measuring instrument, such as a model P53 Analyzer manufactured by GLI International, Inc. of Milwaukee Wis. U.S.A.

The cable 24 extends from the printed circuit board 44 through the plug 20 and cap 24. The plug 20 has a cavity therein which receives a ferrite sleeve 50 through which the cable extends. The ferrite sleeve 50 is a cylindrical tubular body of material with high magnetic permeability that tightly engages the exterior of the cable 50. The ferrite sleeve acts as a load which dampens any high frequency signals that are induced into the conductors of the cable 24, thereby blocking such high frequency signals from reaching the circuit board 44 where they may adversely effect the pH sensor signals.

A reference, or standard, glass electrode 54, that preferably is identical to measuring glass electrode 38, is mounted on the support tube 26 and extends into a first chamber 56 formed between the support tube and the outer tube 12. Grooves are formed in the support tube 26 so that the first chamber 56 extends to the interior end of the sensor tip 14. The first chamber 56 contains a buffer solution having a neutral pH of 7.0. Therefore, the reference glass electrode 54, produces an electrical signal indicating neutral pH.

The sensor tip 14 has an internal second chamber 58 that is filled with an electrolyte solution. The ends of the second chamber 58 are sealed by porous junctions 60 and 62 which respectively isolate the electrolyte solution from the solution being tested and from the neutral pH solution in the first chamber 56. The porous junctions 60 and 62 and the electrolyte solution form a double junction salt bridge that electrically connects the reference glass electrode 54 to the solution being tested while physically isolating those elements. This structure forms a second half cell between the circuit ground electrode 33 and a second electrical lead 64 of the reference glass electrode 54.

The second electrical lead 64 from the reference glass electrode 54 is connected to the printed circuit board 44 and specifically to a second preamplifier 66 located in close proximity to the connection point. The length of the second electrical lead 64 for the reference glass electrode 54 is substantially the same length as the length of the first electrical lead 42 for the measuring glass electrode 38. It is desirable that the leads be substantially the same length so that electrical noise in the vicinity of the pH sensor 10 will equally affect the signals carried by each lead. It will be understood by those skilled in the art, that some variation in the length of one of these leads 42 or 64 with respect the other can be tolerated and still achieve a high degree of immunity to different amounts of electrical noise being induced in the two signals carried by those leads.

The two preamplifiers 46 and 66 for the measuring glass electrode 38 and reference glass electrode 54, respectively, are located substantially the same distances from the point at which the respective electrical leads 42 and 64 from the electrodes connect to the printed circuit board. This further maintains equal lengths of conductors for each signal path at the input side of each preamplifier, so that ambient electrical noise should affect each signal to equivalent degrees.

The circuitry on the printed circuit board 44 produces three output signals representing the pH level sensed by the measuring glass electrode 38, the reference pH level sensed by the reference glass electrode 54, and temperature as measured by the temperature sensor 48. These output signals are applied to separate conductors within the cable 24 which carries the signals to the measuring instrument which determines pH of the unknown solution to which the measuring glass electrode 38 is exposed. This unknown pH value is determined based on a difference between the signal from the measuring glass electrode 38 and the signal from the reference glass electrode 54 that is immersed in a neutral pH solution within the first chamber 56. The measuring instrument also compensates for effects due to temperature variation as measured by temperature sensor 48.

The foregoing description was primarily directed to a preferred embodiment of the invention. Although some attention was given to various alternatives within the scope of the invention, it is anticipated that one skilled in the art, will likely realize additional alternatives. that are now apparent from the disclosure of the embodiments of the invention. Accordingly, the scope of the invention should be determined from the following claims and not limited by the above disclosure.

What is claimed is:

1. A sensor for determining pH of a solution, said sensor comprising:

a housing with a section having an exterior surface for exposure to the solution;

a measuring glass electrode extending through the exterior surface of the section of the housing;

a first preamplifier within the housing;

a first electrical conductor extending between the measuring glass electrode and the first preamplifier for a first distance;

a circuit ground electrode extending through the exterior surface of the section of the housing;

a reference glass electrode supported within the housing;

a second preamplifier within the housing;

a second electrical conductor extending between the reference glass electrode and the second preamplifier for a second distance which is substantially equal to the first distance; and an electrical cable connected to the first preamplifier and the second preamplifier to carry electrical signals from the pH sensor.

2. The pH sensor as recited in claim 1 further comprising a temperature sensor supported by the housing.

3. The sensor as recited in claim 1 further comprising a ferrite sleeve having an aperture through which the cable passes.

4. The sensor as recited in claim 3 wherein the ferrite sleeve is within the housing.

5. The sensor as recited in claim 1 further comprising a salt bridge formed between the reference glass electrode and an external surface of the housing.

6. The sensor as recited in claim 5 wherein the salt bridge comprises a pair of porous junctions with an electrolyte there between.

7. The sensor as recited in claim 6 wherein the housing forms a first chamber that contains a neutral pH solution in contact with the reference glass electrode.

8. The sensor as recited in claim 7 further comprising a salt bridge formed between the first chamber and an external surface of the housing.

9. The sensor as recited in claim 8 wherein the salt bridge comprises a pair of porous junctions with an electrolyte there between.

10. The sensor as recited in claim 1 wherein the circuit ground electrode has a tubular shape with an aperture there through, and the measuring glass electrode is received in the aperture.

11. The sensor as recited in claim 1 further comprising a ferrite member having an aperture through which the cable passes, wherein the ferrite member provides a load which dampens a high frequency signal that is induced into the cable.

12. A sensor for determining pH of a solution, said sensor comprising:

a housing having an outer tube with a first open end and a second open end, wherein the first open end is closed by a sensor tip for exposure to the solution with the sensor tip and the second opened that is closed by a plug, the housing forming a first chamber and the sensor tip having an opening there through;

a circuit ground electrode extending through the opening in the sensor tip and having a tubular shape with an aperture there through and;

a measuring glass electrode received in the aperture of the circuit ground electrode;

an electric circuit within the housing and having a first preamplifier and a second preamplifier;

an electrical conductor connecting the measuring glass electrode to the first preamplifier and having a given length;

a reference glass electrode extending into the first chamber of the housing;

a second electrical conductor connecting the reference glass electrode to the second preamplifier and having a length which is substantially equal to the given length; and an electrical cable connected to the electric circuit to carry electrical signals produced by the sensor.

13. The sensor as recited in claim 12 further comprising a temperature sensor connected to the electric circuit.

14. The sensor as recited in claim 12 further comprising a ferrite sleeve having an aperture through which the cable passes.

15. The sensor as recited in claim 14 wherein the ferrite sleeve is within the housing.

16. The sensor as recited in claim 12 wherein the sensor tip defines a second chamber containing an electrolyte, wherein the second chamber is separated from the first chamber by a first porous junction and is separated from an exterior of the sensor tip by a second porous junction.

17. The sensor as recited in claim 12 wherein the first chamber contains a neutral pH solution.

18. The sensor as recited in claim 12 wherein the tubular circuit ground electrode, the reference glass electrode, and the electric circuit are,supported by a support tube that is received within the housing.

19. The sensor as recited in claim 18 wherein the support tube partially defines the first chamber within the housing.

20. The sensor as recited in claim 12 further comprising a ferrite member having an aperture through which the cable passes, wherein the ferrite member provides a load which dampens a high frequency signal that is induced into the cable.

* * * * *